United States Patent [19]
Thompson et al.

[11] Patent Number: 5,141,312
[45] Date of Patent: Aug. 25, 1992

[54] FIBER OPTIC PHOTOLUMINESCENCE SENSOR

[75] Inventors: Richard B. Thompson, Baltimore, Md.; Michael Levine, Dallas, Tex.

[73] Assignee: The United States of America as represented by the Secretary of the Navy, Washington, D.C.

[21] Appl. No.: 531,721

[22] Filed: Jun. 1, 1990

[51] Int. Cl.$^5$ .............................. G01J 1/42
[52] U.S. Cl. ......................... 356/218; 356/342; 356/221; 356/28; 250/227.11; 385/33
[58] Field of Search ............... 356/213, 218, 221, 226, 356/73.1, 445, 300, 301, 246, 44, 48, 28, 5, 217; 250/227.11, 227.23

[56] References Cited

U.S. PATENT DOCUMENTS

| | | | |
|---|---|---|---|
| Re. 33,424 | 11/1990 | Noguchi et al. | 356/446 |
| 3,986,775 | 10/1976 | Chang et al. | 356/301 |
| 4,154,529 | 5/1979 | Dyott | 250/227.11 |
| 4,368,047 | 1/1983 | Andrede et al. | 436/517 |
| 4,447,546 | 5/1984 | Hirschfeld | 356/445 |
| 4,533,246 | 8/1985 | Braun | 356/317 |
| 4,582,809 | 4/1986 | Block et al. | 356/445 |
| 4,712,912 | 12/1987 | Messerschmidt | 356/300 |
| 4,775,637 | 10/1988 | Sutherland et al. | 356/246 |

Primary Examiner—Richard A. Rosenberger
Assistant Examiner—Hoa Pham
Attorney, Agent, or Firm—Thomas E. McDonnell; George Jameson

[57] ABSTRACT

A photoluminescence sensor for detecting a photoluminescent light from a photoluminescent material is disclosed. In a preferred embodiment the photoluminescence sensor comprises: a source of light; a concave mirror having at least one perforation for passing the source light through the at least one perforation; an optical waveguide having proximal and distal ends with the photoluminescent material being disposed at the distal end; an objective for directing the source light into the proximal end of the waveguide; an objective for receiving photoluminescent light and for focusing the photoluminescent light onto the perforated concave mirror; a liquid filter for passing the photoluminescent light reflected from the perforated concave mirror to a detector to detect the photoluminescent light. The sensor can also include a chopper disposed at the output end of the objective for modulating the light source at a select frequency and a lock-in amplifier tuned to measure the output from the detector at the select frequency.

14 Claims, 1 Drawing Sheet

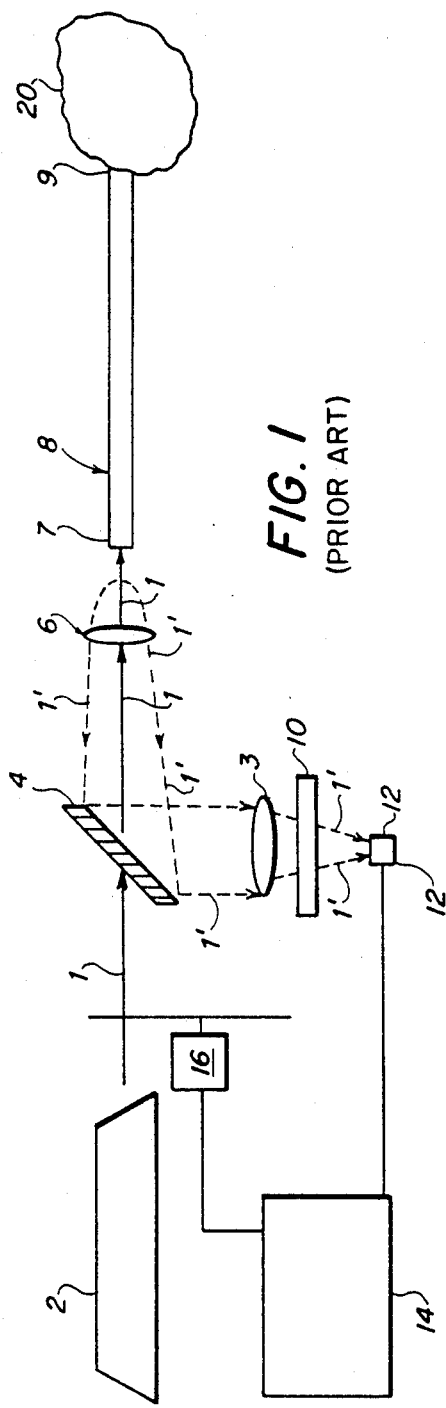
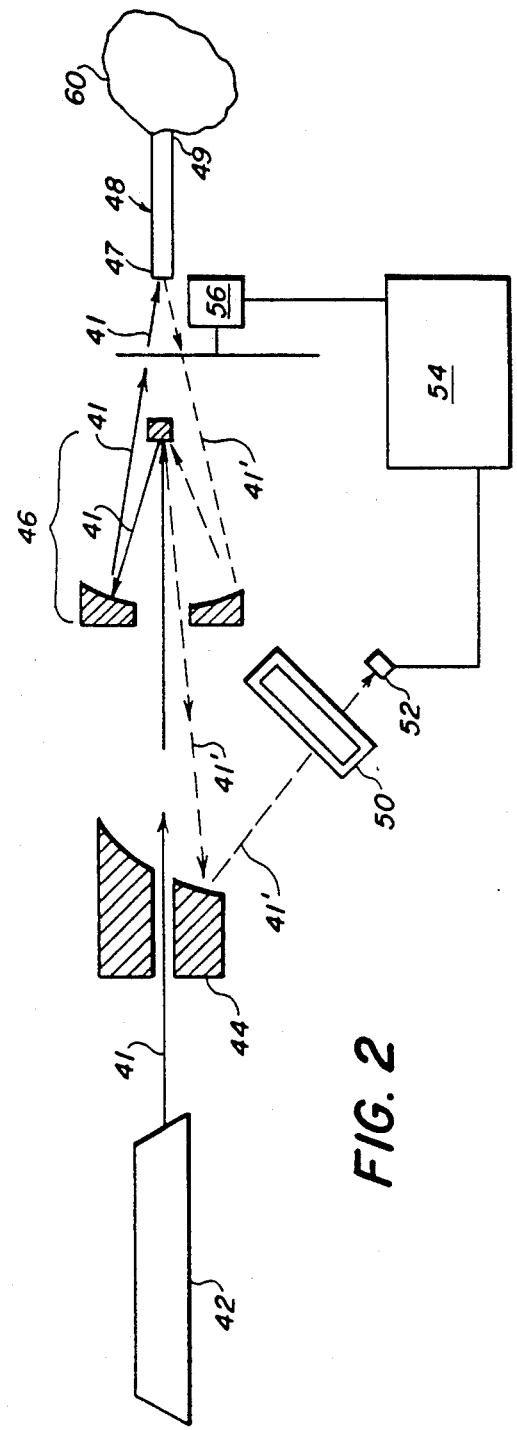
FIG. 1 (PRIOR ART)
FIG. 2

FIBER OPTIC PHOTOLUMINESCENCE SENSOR

BACKGROUND OF THE INVENTION

1. Field of the Invention

The invention relates to detecting and quantitating molecules or influences and more particularly to an improved fiber optic photoluminescence sensor.

2. The Prior Art

The use of fiber optics in conjunction with photoluminometry is growing in fields as diverse as biophysics, remote sensing, immunodiagnostics, and chemical process monitoring. Photoluminescence is a well developed, powerful, and versatile technique for chemical or influence (i.e., temperature, pressure, etc.) sensing. Photoluminescence is a broad term which includes fluorescence, phosphorescence, Raman scattering, etc. The intrinsic wavelength difference between excitation and emission makes photoluminescence well suited for use with fiber optics. Fiber optics themselves have unique attributes which make them ideal for many sensing applications. Fiber optics permit remote, continuous monitoring of analytes in hazardous environments, and in the presence of electromagnetic interference or flammable atmospheres. Fiber optics are small and lightweight, making them useful on air-and spacecraft. Fibers have enormous information-carrying capacity due to the THz bandwidth of light, and signals of different colors can travel in the same fiber without interference. The hope (or necessity) of utilizing these advantages has fueled the development of fiber optic sensors employing photoluminometry.

The fundamental idea of photoluminescence-based sensors is to detect an analyte or influence by a change in the photoluminescence of a susceptible material. Several instrument configurations for performing photoluminometric measurements through fiber optics have been described in the literature, using a great variety of photoluminescence observables (intensity, spectra, lifetimes) and configurations for the sensing tip (evanescent wave or distal cuvette). Basically, as shown in the prior art photoluminescence sensor apparatus of FIG. 1, a susceptible photoluminescent material 20 localized at the distal end 9 of an optical fiber is excited by light coming down the optical fiber 8, and its photoluminescence is coupled back into the fiber 8, separated from the excitation, and observed at the proximal end 7 of the fiber 8. In FIG. 1, the solid line/arrows 1 represents the path of the exciting light, while the dashed line/arrows 1' represents the path of photoluminescence.

All fiber optic photoluminescence sensors have a light or excitation source 2, some means for coupling or coupling lens 6 the light into the fiber 8, a photoluminescent material 20 localized at the distal end 9, a means for separating the emission from the excitation 4, and a detector or photodetector 12 (FIG. 1). Fiber optics impose constraints on the optical configuration performing these functions that are not encountered in ordinary photoluminescence sensors, and which require attention to assure optimum performance. For instance, the positions of the excitation source 2, the coupling lens 6 and the proximal fiber end 7 along some axes must be controlled with micrometer precision, which is seldom required in a typical photoluminescence sensor. Also, fiber optic photoluminescence sensors are generally less sensitive than standard research grade photoluminescence sensors, and thus it is important to get the best performance out of the former; this seems to be particularly true for those using a waveguide binding (evanescent wave) sensing tip.

Various types of fiber optic photoluminescence sensors have been proposed (see U.S. Pat. Nos. 4,775,637; 4,582,809; and 4,447,546). Generically, such sensors consist of a light source 2 (FIG. 1), whose exciting light passes through a (spatially or spectrally) filtering mirror 4 and is focused into the fiber 8 by an objective 6 at the proximal end 7 of the fiber 8. The fiber 8 conducts the exciting light to the distal end 9 of the fiber 8, where the photoluminescent material 20 is present or is attached to the end of the fiber 8, where the exciting light is absorbed. The photoluminescent material 20 emits its characteristic emission, which re-enters the fiber 8 (the same fiber need not be used, but typically is) and is conducted back to the proximal end 7 of the fiber 8, where it passes through the objective 6, is reflected off the mirror 4 through a lens 3 and a filter 10 into the photodetector 12. Essentially all the fiber optic photoluminescence sensors described in the literature use this basic scheme, and differ in the details of the components used and their arrangement. For instance, some photoluminescence sensors in the prior art use separate optical fibers to carry the excitation and emission; such sensors have no mirror to separate excitation from emission, but require two objectives, one to direct the excitation into one fiber, and the other objective to receive the emission and focus it onto the detector. Many of the sensors described in the literature are insufficiently sensitive to detect many of the chemical analytes of interest, including pollutants, drugs, and poisons. The improvements described below are aimed at increasing the sensitivity of detecting any analyte or influence, irrespective of the distal end configuration (distal cuvette or waveguide binding), actual sensing chemistry, or wavelengths involved.

Typically, the mirror 4 is a dichroic mirror coated and oriented to pass the exciting light and reflect the (longer wavelength) photoluminescence emission into the detector 12 (or vice versa). Such mirrors have the disadvantages that they are not useful over a broad wavelength range, are a source of background photoluminescence, and have poor transmission. Andrade et al. (U.S. Pat. No. 4,368,047) used a perforated planar mirror to pass the narrow beam of a laser for excitation, and reflect the more broadly spread photoluminescence as it comes back out of the objective 6, towards the detector 12. Braun (U.S. Pat. No. 4,533,246) also discloses the use of a perforated planar mirror. The disadvantage of this is that it requires a separate lens 3 to focus the photoluminescence on the detector 12, which adds weight, complexity, insensitivity, and a propensity for misalignment to the sensor.

The purpose of the filter 10 in FIG. 1 is to block scattered shorter wavelength exciting light from entering the detector 12 and being confused with authentic (signal) photoluminescence. Such light scattered off the coupler or other components can be orders of magnitude stronger than the actual photoluminescence, and can seriously degrade the performance of the sensor. The colored glass or interference filters well known to the art will ordinarily serve in this respect. Unfortunately, nearly all of these filters themselves photoluminesce appreciably when struck by scattered exciting light, and this photoluminescence can be sensed as authentic sample photoluminescence.

The use of a chopper 16 or other light modulator together with a lock-in amplifier 14 or other phase-sensitive detector is well known in the art for improving the detectability of weak signals, such as in fiber optic sensors. Thus, a chopper 16 placed in the beam of exciting light will modulate it at a particular frequency, and the lock-in amplifier 14 can be tuned to measure the detector 12 output at only that frequency, eliminating spurious noise at other frequencies. Ordinarily, the chopper 16 is placed as closely to the light source 2 as is convenient.

Many sorts of lenses or objectives have been used to launch light into fiber optics, including gradient index rod lenses, simple lenses, spherical lenses, and most often, refracting microscope objectives. All of these optics are transmissive, and therefore suffer from two drawbacks: most transmit ultraviolet light poorly, and due to their transmissive nature they can photoluminesce when light passes through them. Ultraviolet excitation is very useful for detecting many photoluminescent molecules.

Many kinds of light detectors have been used to detect the photoluminescence signals. They include photomultipler tubes, PIN photodiodes, avalanche photodiodes, and phototransistors. Their usefulness is mainly determined by their sensitivity, which is well known in the art.

The advantages of fiber optical photoluminescence sensors per se are well known: they permit continuous monitoring of a variety of chemical analytes under circumstances inhospitable to conventional analytical chemical techniques or instrumentation. For instance, fiber optic photoluminescence sensors have been designed to sense carbon dioxide or pH in the bloodstream, pollutants deep underground, or toxic chemicals in the air. All of them have the same functional requirements as outlined in FIG. 1, although they differ in detail, and selection of components.

SUMMARY OF THE INVENTION

Accordingly, it is an object of the present invention to provide a fiber optic photoluminescence sensor which overcomes the deficiencies of the prior art.

Another object of the present invention is to provide a photoluminescence sensor with improved performance over those of the prior art.

Another object of the present invention is to utilize a concave mirror having at least one perforation for passing light through that perforation.

Another object of the present invention is to provide a reflecting microscope objective of a Schwarzchild type.

Another object of the present invention is to provide a chopper and a lock-in amplifier where the chopper is located close to the proximal end of the fiber.

Another object of the present invention is to provide a liquid filter for preventing scattered exciting light from entering the detector.

Another object of the present invention is to provide a photoluminescence sensor for use in a wide array of apparatus including but not limited to an immunoassay apparatus.

A further object of the present invention is to provide a photoluminescence sensor comprising a laser source of light directed through a perforation in a concave mirror, after which the light is focused by a Schwarzchild type reflecting microscope objective through a light modulating chopper and into an optical fiber at the end of which the light is absorbed and photoluminescence is emitted from some susceptible material. The photoluminescent light returns through the fiber, or another fiber, and reversely through the reflecting microscope objective, which sends the photoluminescent light onto the perforated concave mirror which, in turn, focuses the light through a liquid filter onto a detector.

This invention provides for reduction in noise produced by photoluminescence, including fluorescence, the Raman effect, phosphorescence and photoluminescence in mirrors, refracting lenses, and glass fiber elements.

BRIEF DESCRIPTION OF THE DRAWINGS

FIG. 1 is a schematic representation of a typical prior art photoluminescence sensor apparatus.

FIG. 2 is a schematic representation of a preferred embodiment of the present invention.

DETAILED DESCRIPTION OF THE PREFERRED EMBODIMENT

FIG. 2 shows a schematic representation of the preferred embodiment of the present invention. The present invention comprises four novel features which can be used either singly as a new part added to prior art set ups or preferably all four features are used in combination as added new parts to the prior art set ups. The four novel features are the following:

(1) a perforated concave mirror 44;
(2) a reflective objective 46;
(3) the placement of a chopper 56 near the proximal end 47 (or the distal end 49) of an optical fiber or optical waveguide 48; and
(4) a liquid filter 50. The advantages of each novel feature will be brought out in the rest of this description.

The features of a preferred embodiment of the present invention include a light source 42, preferably a laser, as the source of the exciting light.

As mentioned above, the first novel feature, a perforated concave mirror 44 is used. The advantage of such a mirror 44 is that the exciting light is permitted to pass through the perforation in the mirror 44 while returning photoluminescence is focused by the mirror 44 onto a detector 52. The mirror 44 can have any surface which focuses light such as spherical, aspheric, or an off-axis paraboloid, all with holes drilled through them, preferably one to two millimeters in diameter, to allow laser excitation to pass.

The second novel feature is a reflecting microscope objective 46 which is used to launch light from the mirror 44 into an optical fiber or optical waveguide 48. The launcher is a means to direct light into the optical fiber 48 so that it is transmitted and contained within the fiber 48 by total internal reflection. The reflecting microscope objective 46 is preferably of the Schwarzchild design. These objectives 46, which have been known for many years, pass ultraviolet light well (indeed, are largely wavelength independent) and photoluminesce very little. The objective 46 is preferably used with the fiber axis aligned approximately 20° to the objective axis to assure the collection of the photoluminescence from the proximal end of the fiber 48. The objective of this invention may also comprise two separate components, one used for sending light to the material 60 and a second for receiving photoluminescent light from the material 60.

The third feature of the present invention is placement of a chopper 56 in a novel location between the reflective objective 46 and the proximal end 47 of the fiber 48. The chopper 56 can be any device which will modulate the intensity of the light. Thus, the exciting light, which hits other optical components, such as the mirror 44 and objective 46, remains unmodulated until it reaches the fiber's proximal end 47. Thus, scattered exciting light or particularly the photoluminescence it excites in optical components, such as the mirror 44 and objective 46, is also unmodulated and is discriminated against by the lock-in amplifier 54. This background photoluminescence is an important source of noise and can degrade sensitivity. Simply placing the chopper between the filter 50 and the detector 52 does not have this effect.

The fourth novel component of the present invention is the use of a liquid filter 50 to block scattered shorter wavelength exciting light from entering the detector 52 and being confused with authentic photoluminescence. The liquid filter 50 is preferably a low photoluminescence fused silica cuvette filled with a 1% solution of potassium dichromate or other colored solute in distilled water or other transparent, photoluminescent solvent. Liquid filters have much lower intrinsic photoluminescence than the solid glass filters commonly used.

The operation of a preferred embodiment of the photoluminescence sensor of the present invention is the same as that of the prior art except for the inclusion of the four novel components of the invention. Exciting light from the light source 42, following a path represented by the solid line/arrow 41, passes through the perforation in the first novel component, the perforated concave mirror 44, to the second novel component, the reflecting objective 46, where it is then modulated by chopper 56 the placement of which in this particular location makes up the third novel component. After being modulated by chopper 56, the exciting light is then passed into the proximal end 47 of fiber 48. The fiber 48 conducts the exciting light to the distant end 49 of fiber 48, where the photoluminescent material 60 is present or is attached thereto. This photoluminescent material 60 absorbs the exciting light at the distal end 49 of the fiber 48. The fiber 48 acts as a waveguide, and it should be noted that other waveguides may be used with this invention. The optical waveguide may be a bundle of fibers or a slab waveguide, and single or multimode. The fibers may be of different transparent materials, including glass, plastic, fused silica and the like. The photoluminescent material 60 emits its characteristic photoluminescence, which reenters the distal end 49 of the fiber 48, although the same fiber need not be used, and is conducted back to the proximal end 47 of the fiber 48. The light, following the path represented by the dashed line/arrow 41', is then reversely conducted through reflecting objective 46. The light is then reflected off of perforated concave mirror 44, which focuses the returning photoluminescence through a liquid filter 50 and onto detector 52. Filter 50 makes up the fourth novel component of the present invention. The liquid filter 50 blocks scattered shorter wavelength exciting light from entering the detector 52 and being confused with authentic photoluminescence. Liquid filters have much lower intrinsic fluorescence than the solid glass filters commonly used.

The reflecting objective 46 is used to insert the light into and receive light from fiber optic 48. However, two separate components may be used as objectives for launching light into a photoluminescent material 60 and for receiving photoluminescent light from such a sample, perhaps through a second optical fiber.

Although there are many components and systems available to do the same type of sensing as the present invention, it has been found that the arrangement of the components and apparatus of the present invention provide improved results over the prior art.

The source 42 may be a laser such as a Liconix 4214NB HeCd (Sunnyvale, CA 94089) laser which produces 12 milliwatts at 442 nm. The source 42 can also be a lamp or light emitting diode, but the laser is the preferred source because it produces a highly collimated, intense, monochromatic light.

The perforated concave mirror 44 selected was an off-axis parabolic mirror (catalog number MP-40Y-14) which was produced by Optics For Research (Caldwell, NJ 07006). This perforated concave mirror additionally acts as a spatial filter which filters out incoherent, poorly collimated plasma lines from the exciting laser beam. The perforation passes only coherent laser beam light.

The reflecting objective 46 may be a 15×0.28 NA reflecting (Schwarzchild) microscope objective produced by Ealing (Holliston, MA 01746). The reflecting objective 46 launches excitation into the fiber 48. Objective 46 focuses the laser beam on the proximal end 47 of the optical fiber or waveguide 48. The Schwarzchild reflecting objective 46 is wavelength independent and has low photoluminescence. There is a large working distance between the objective 46 and the proximal end 47 of the waveguide 48. This large working distance permits installation of the chopper 56 at the input of the fiber 48 (between the fiber 48 and the reflecting objective 46).

It has been found that the chopper 56 should be placed as close as possible to the photoluminescent material 60. Usually, the most convenient location is between the objective 46 and the proximal end 47 of the fiber or waveguide 48. However, if conditions permit, the chopper 56 could be placed at the distal end 49 of the fiber or waveguide 48. The closer the chopper 56 is to the material 60 being tested, the less noise from the light source is present.

The photoluminescence exiting the fiber 48 is spread out by passing through the objective 46 prior to striking the surface of the perforated concave mirror 44. The spread out light 41' from the material 60 striking the concave mirror 44 permits capture of the photoluminescence light, with very little loss through the perforation and back to the source 42. The concave mirror 44 reflects most of the photoluminescence, and is wavelength independent. The mirror 44 also does not photoluminesce itself, and focuses the photoluminescence onto a detector 52 without the introduction of additional photoluminescence by a focusing lens to the detector 52.

The liquid filter 50 may be a 50×50×3 mm liquid filter which was produced by NSG Precision cells (Farmingdale, NY 11735). In this case the cuvette was made of synthetic fused silica (chosen for its low photoluminescence) to the same dimensions as ordinary glass filters and filled with a 1% aqueous solution of $K_2CR_2O_7$. This solution is totally nonfluorescent, and effective in blocking the laser light. This tactic is also applicable at other wavelengths, since the liquid filter can simply be refilled with another absorbing solution.

The liquid filter 50 was filled with an appropriate absorbing solution which blocked scattered excitation from reaching the detector 52. The liquid filter 50 also provided the lowest photoluminescence as compared with interference filters or glass filters.

The detector 52 in the preferred embodiment may be a high sensitivity R928 photomultiplier tube produced by Hamamatsu (Bridgewater, NJ 08807), together with a suitable low noise power supply.

Signal amplification and processing were performed by an exemplary Stanford Research Systems (Sunnyvale, CA 94089) lock-in amplifier 54 connected to a chopper 56 from the same manufacturer. The chopper 56 was the modulator of the light.

The waveguide or fiber optic fibers were soft plastic-clad silica fibers with 200 or 600 micron core diameters having low background photoluminescence. These fibers were obtained from General Fiber Optics (Cedar Grove, NJ 07009) (0.38 NA) or Quartz et Silice (Cedex 27, 92096 Paris, France) (0.40 NA).

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A photoluminescence sensor for detecting a photoluminescent light from a photoluminescent material, said sensor comprising in combination:
   a source of light;
   a concave mirror having at least one perforation for passing said source light through said at least one perforation;
   an optical waveguide having proximal and distal ends, said photoluminescent material being disposed at said distal end;
   an objective for directing said source light into said proximal end of said waveguide;
   an objective for receiving photoluminescent light and for focusing said photoluminescent light onto said perforated concave mirror;
   means for passing said photoluminescent light reflected from said perforated concave mirror;
   a detector for detecting said photoluminescent light from said passing means;
   a chopper, disposed at the output of said objective, for directing and modulating said source light at a select frequency; and
   a lock-in amplifier tuned to measure an output from said detector at said select frequency.

2. The sensor of claim 1 wherein said chopper is located at the proximal end of said waveguide.

3. A photoluminescence sensor comprising in combination:
   a source of light having an output;
   an optical waveguide having proximal and distal ends and having a photoluminescent material at said distal end;
   means for collecting a photoluminescent light;
   a reflecting microscope objective for directing said source light into said optical waveguide to cause said photoluminescent material to transmit said photoluminescent light back into said optical waveguide and for focusing said photoluminescent light from said optical waveguide;
   means for detecting said photoluminescent light;
   a filter for preventing scattered exciting light from entering said detecting means;
   a chopper, disposed at the output end of said objective, for modulating said source light at a select frequency; and
   a lock-in amplifier tuned to measure an output from the detector means at said select frequency.

4. The sensor of claim 3 wherein said chopper is located at said proximal end of said waveguide.

5. A photoluminescence sensor comprising in combination:
   a source of light;
   an optical waveguide having proximal and distal ends and having a photoluminescent material at said distal end for providing photoluminescent light;
   means for collecting said photoluminescent light;
   an objective for directing said source light into the proximal end of said optical waveguide;
   an objective for receiving said photoluminescent light and for focusing said photoluminescent light onto said means for collecting;
   a liquid filter for substantially only passing said photoluminescent light;
   a detector for detecting said photoluminescent light from said filter;
   a chopper disposed at the output of said objective for modulating said source light at a select frequency; and
   a lock-in amplifier tuned to measure the detector output at said select frequency.

6. The sensor of claim 5 wherein said chopper is located at the proximal end of said waveguide.

7. A photoluminescence sensor comprising in combination:
   a source of light;
   an optical waveguide having proximal and distal ends and having a photoluminescent material at said distal end;
   means for collecting a photoluminescent light coming from said optical waveguide;
   an objective for directing said source light into said proximal end of said optical waveguide to cause said photoluminescent material to emit said photoluminescent light;
   an objective for receiving photoluminescent light from said waveguide and for focusing said photoluminescent light onto said means for collecting;
   a liquid filter for substantially only passing said photoluminescent light reflected from said collecting means;
   a detector for detecting said photoluminescent light from said filter;
   a chopper, located between said objectives and said waveguide, for modulating said light at a select frequency; and
   a lock-in amplifier tuned to measure an output from said detector at said select frequency.

8. The sensor of claim 7 wherein said objective for directing and said objective for receiving and focusing are the same objective.

9. The sensor of claim 8 wherein said same objective is a reflecting microscope objective.

10. The sensor of claim 9 wherein said reflecting microscope objective is of the Schwarzchild type.

11. The sensor of claim 7 wherein said means for collecting is an interference filter.

12. The sensor of claim 7 wherein said means for collecting is a dichroic mirror coated and oriented to pass said source light and reflect said photoluminescence light into said detector.

13. The sensor of claim 7 wherein the light source is a laser.

14. A photoluminescence sensor comprising:
a laser source of light;
a concave mirror having at least one perforation for passing said source light through said at least one perforation;
an optical waveguide having distal and proximal ends and having a photoluminescent material at said distal end;
a Schwarzchild type reflecting microscope objective for directing said source light into said optical waveguide, and for receiving photoluminescent light emitted by said waveguide and for focusing said photoluminescent light onto said concave mirror;
a detector for detecting said photoluminescent light reflected from said concave mirror;
a liquid filter for preventing scattered light from entering said detector;
a chopper, disposed at the source light output of said reflecting microscope, for modulating said source light at a select frequency; and
a lock-in amplifier tuned to measure an output from said detector at said select frequency.

* * * * *